US006651655B1

(12) United States Patent
Licalsi et al.

(10) Patent No.: US 6,651,655 B1
(45) Date of Patent: Nov. 25, 2003

(54) INHALED VACCINES

(75) Inventors: Cynthia Licalsi, San Diego, CA (US); Gary Ward, San Diego, CA (US); Bernard Greenspan, San Diego, CA (US); Clyde Witham, San Diego, CA (US)

(73) Assignee: Quadrant Technologies Limited, Nottingham (GB)

( * ) Notice: Subject to any disclaimer, the term of this patent is extended or adjusted under 35 U.S.C. 154(b) by 0 days.

(21) Appl. No.: 09/562,798

(22) Filed: May 2, 2000

Related U.S. Application Data

(60) Provisional application No. 60/176,525, filed on Jan. 18, 2000, provisional application No. 60/176,530, filed on Jan. 18, 2000, and provisional application No. 60/176,587, filed on Jan. 18, 2000.

(51) Int. Cl.[7] .......................... A61M 15/00; A61L 9/04

(52) U.S. Cl. .................................... 128/203.15; 424/45

(58) Field of Search ....................... 128/200.12, 200.14, 128/200.22, 200.23, 203.12–203.15, 203.21–203.28, 202.18, 205.13, 205.21, 204.13; 604/58, 62; 424/45, 46, 499; 514/2, 3

(56) References Cited

U.S. PATENT DOCUMENTS

| | | | | | |
|---|---|---|---|---|---|
| 2,798,835 | A | * | 7/1957 | Markham et al. | 167/78 |
| 2,798,836 | A | * | 7/1957 | Bird et al. | 424/45 |
| 3,809,084 | A | * | 5/1974 | Hansen | 128/266 |
| 4,036,223 | A | * | 7/1977 | Obert | 128/266 |
| 5,049,388 | A | * | 9/1991 | Knight et al. | 424/450 |
| 5,492,112 | A | | 2/1996 | Mecikalski et al. | |
| 5,577,497 | A | * | 11/1996 | Mecikalski et al. | 128/203.15 |
| 5,622,166 | A | | 4/1997 | Eisele et al. | |
| 5,626,871 | A | * | 5/1997 | Makino et al. | 424/451 |
| 5,645,051 | A | | 7/1997 | Schultz et al. | |
| 5,683,697 | A | * | 11/1997 | Tani | 424/735 |
| 5,921,237 | A | | 7/1999 | Eisele et al. | |
| 5,942,242 | A | * | 8/1999 | Mizushima et al. | 424/434 |
| 5,952,008 | A | | 9/1999 | Backstrom et al. | |
| 5,994,314 | A | | 11/1999 | Eljamal et al. | |
| 6,211,162 | B1 | * | 4/2001 | Dale et al. | 514/44 |
| 6,347,629 | B1 | * | 2/2002 | Braithwaite | 128/203.15 |
| 6,398,774 | B1 | * | 6/2002 | Penner et al. | 604/514 |
| 6,419,900 | B2 | * | 7/2002 | Placke et al. | 424/45 |
| 6,475,467 | B1 | * | 11/2002 | Keller et al. | 424/45 |
| 6,484,717 | B1 | * | 11/2002 | Dagsland et al. | 717/173 |
| 6,488,648 | B1 | * | 12/2002 | Matsugi et al. | 604/57 |
| 6,503,480 | B1 | * | 1/2003 | Edwards et al. | 424/45 |
| 2002/0037316 | A1 | * | 3/2002 | Weers et al. | 424/450 |
| 2002/0159954 | A1 | * | 10/2002 | Small et al. | 424/46 |
| 2002/0164290 | A1 | * | 11/2002 | Stefely et al. | 424/45 |

FOREIGN PATENT DOCUMENTS

| | | |
|---|---|---|
| WO | WO 93/21950 | 11/1993 |
| WO | WO 01/56640 | 8/2001 |

OTHER PUBLICATIONS

Levine, M., Woodrow, G., Kaper, J., Cobon, G. (1997). New Generation Vaccines, pp. 25–34 New York. Marcel Dekker, Inc.*

Fox, J. (1994, Feb.). No winners agains AIDS. Bio/Technology, vol. 12, pp. 128.*

Spitler, L. (1995). Editoriial. Cancer Vaccines: The Interferon Analogy. Cancer Biotherapy, pp. 1–3.*

(List continued on next page.)

*Primary Examiner*—Weilun Lo
*Assistant Examiner*—Teena Mitchell
(74) *Attorney, Agent, or Firm*—Perkins Coie LLP

(57) ABSTRACT

In a method for creating an immune response, a vaccine is prepared in the form of a dry powder. The powder particles have an aerodynamic particle size range from 1–100 microns. A dose of powder is loaded into a dry powder inhaler. The dose is inhaled with an inspiratory flow rate of less than 60 liters per minute. A mucosal immune response is created via particles of the vaccine material depositing on the upper respiratory tract. A systemic immune response is created via particles of the vaccine material depositing into the deep lung. The vaccine material is size reduced by e.g., jet milling, into the desired range, yet vaccine potency is retained.

29 Claims, 2 Drawing Sheets

OTHER PUBLICATIONS

Fomsgaard, A. (1999, Jan.). HIV–1 DNA vaccines. Immunology Letters, 65 (1–2): pp 127–131 Abstract only.*

Vogel, F. (1995). The role of adjuvants in retroviral vaccines. International Jounal of Immunopharmacology 17 (2). pp 85–90. Abstrat only.*

Haynes, B., Putman, S., Weinberg, J. (1996). Update on the issues of HIV vaccine development. Annals of Medicine 28 (1). pp. 39–41. Abstract only.*

Blinkova, et al., A possibility of reduction of a session of aerosol immunization with dry live plague vaccine, *Zh Mikrobiol Epidemiol Immunobiol*, 8:42–5 (1975), (Russian with English translation included).

Cutts et al., Alternative routes of measles immunization; a Review, *Biologicals*, 25:323–338 (1997).

Dilraj et al., Response to different measles vaccine strains given by aerosol and subcutaneous routes to schoolchildren: a randomised trial; *The Lancet*, 355:798–803 (2000).

Egorova, et al., Immunobiologic parallels in the study of dry and liquid aerosol vaccines in experiments on animals. I. Immunogenic and anaphylactogenic properties of dry and liquid vaccine of tetanus anatoxin, *Zh Mikrobiol Epidemiol Immunobiol*, 46(9):60–66 (1969), (Russian with English translation included).

Fediaev, S.F., Use of the RSP–1M apparatus in aerosol immunization of humans with dry plague vaccine, *Zh Mikrobiol Epidemiol Immunobiol*, 4:82–85 (1975), (Russian with English translation included).

Fediaev, S.F., Some problems concerning the methods of study of aerosols of dry vaccine preparations, *Zh Mikrobiol Epidemiol Immunobiol*, 49(11):92–96 (1972), (Russian with English translation included).

Fontanges, et al., Aerosol Immunization. I. Construction of a new climate–controlled experimental chamber, *Annales de l'Institut Pasteur*, 114(5) 608–623 (1968), (French with English translation included).

Fontanges, et al., Aerosol Immunization, II. Experimental study of a new climate–controlled experimental Chamber, *Annales de l'Institut Pasteur*, 114(5):624–631 (1968), (French with English translation included).

Fontanges, et al., Aerosol Immunization, III. Devices for production and control of powder antigen aerosols, *Ann. Inst. Pasteur*, 118:806–814 (1970), (French with English translation included).

Fontanges et al., Aerosol Immunization, IV. Improvement of vaccine aerosol production devices, *Ann. Inst. Pasteur*, 118:815–824 (1970), (French with English translation included).

Fontanges et al., Aerosol Immunization, V. Kinetic study of lyophilized bacteria aerosol in a climate–controlled experimental chamber, *Annales de l'Institut Pasteur*, 119(2): 151–171 (1970), (French with English translation included).

Fontanges et al., Aerosol Immunization, VI. Vaccination of baboons with lyophilized diphtheria anatoxin, *Ann. Inst. Pasteur*, 119:172–192 (1970), (French with English translation included).

Fontanges et al., Aerosol Immunization, VII. Vaccination of baboons with lyophilized tetanus anatoxin and with a mixture of tetanus and diphtheria anatoxins, *Ann. Inst. Pasteur*, 120: 831–848 (1971), (French with English translation included).

Fournier, et al., Experimental subcutaneous and aerosol vaccination of baboons against the plague. Lack of correlation between hemagglutinating or precipitating antibodies and protection, *Annales Microbiol. (l'Institut Pastuer)* 124B:315–328 (1973), (French with English translation included).

Fournier, et al., Dry aerosol vaccination against newcastle disease I. Safety and activity controls on chickens, *14th Congress of the International Assoc. of Biological Standardization*, 33:269–272 (1976).

Gerasimov, et al.., Device for administering powdery medical preparation; *Zhurnal ushnykh, nosovykh gorlovtjg boleznei*; 2:120–121 (1975) (Russian with English translation included).

Hers, et al., Airborne transmission and airborne infection, Concepts and methods presents at the VIth International Symposium on Aerobiology, Halsted Press Book pp. 295–345(1973).

Romanov, V.L., Study of Immunological effectiveness of live dry aerosol influenza vaccine, *Zh Mikrobiol Epidemiol Immunobiol*, 3:122–123, (1976), (Russian with English translation included).

Romanov, V.L., Study of Reactogenicity and innocuousness of live dry aerosol influenza vaccine, *Zh Mikrobiol Epidemiol Immunobiol*, 3:124–125 (1976) (Russian with English translation included).

Sabin, Albert B., My last will and testament on rapid elimination and ultimate global eradication of poliomyelitis and measles, *Pediatrics*, 90(1): 162–169 (1992).

Semin, S.D., The effectiveness of dry virus vaccine GNKI against Aujesky's disease, *Veterinariia*, 7:52–54 (1971) (Russian with English translation included).

Vorontsov et al., Study of the reactogenic action and efficacy of aerosol immunization with powder divaccine against typhus abdominalis and tetanus, *Voen Med Zh*, 4:55–59 (1967), (Russian with English translation included).

Wigley et al., Aerosol immunization of humans with tetanus toxid, *The Journal of Immunology*, 103(5):1096–1098 (1969).

* cited by examiner

Fig. 1
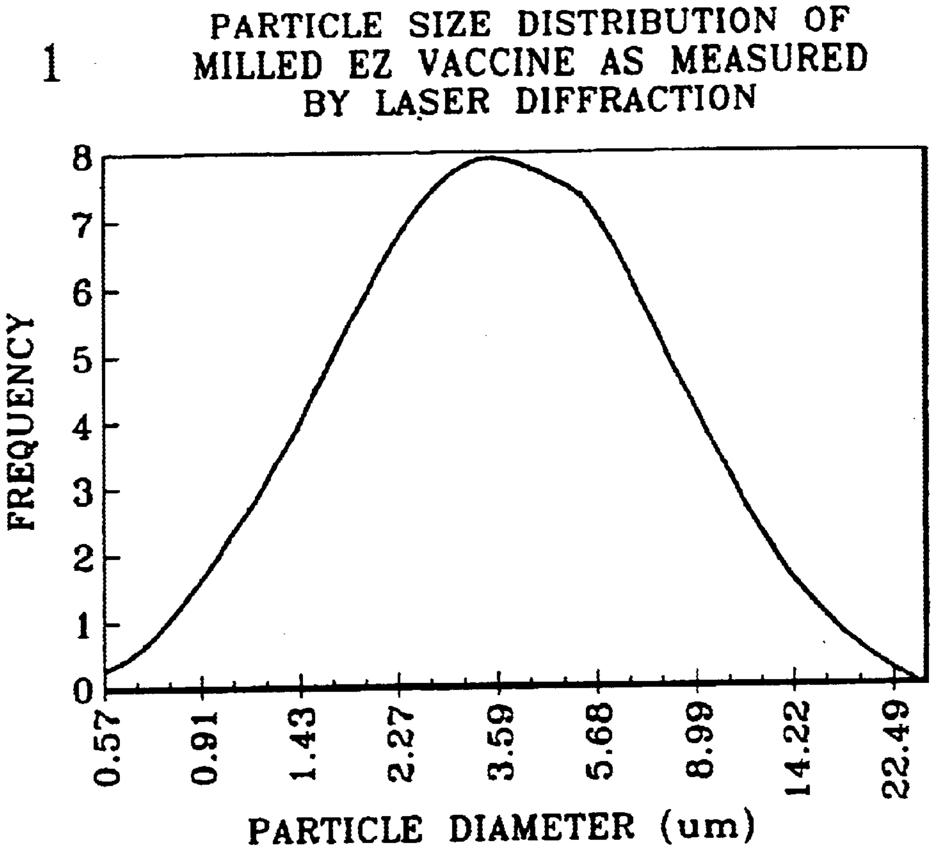
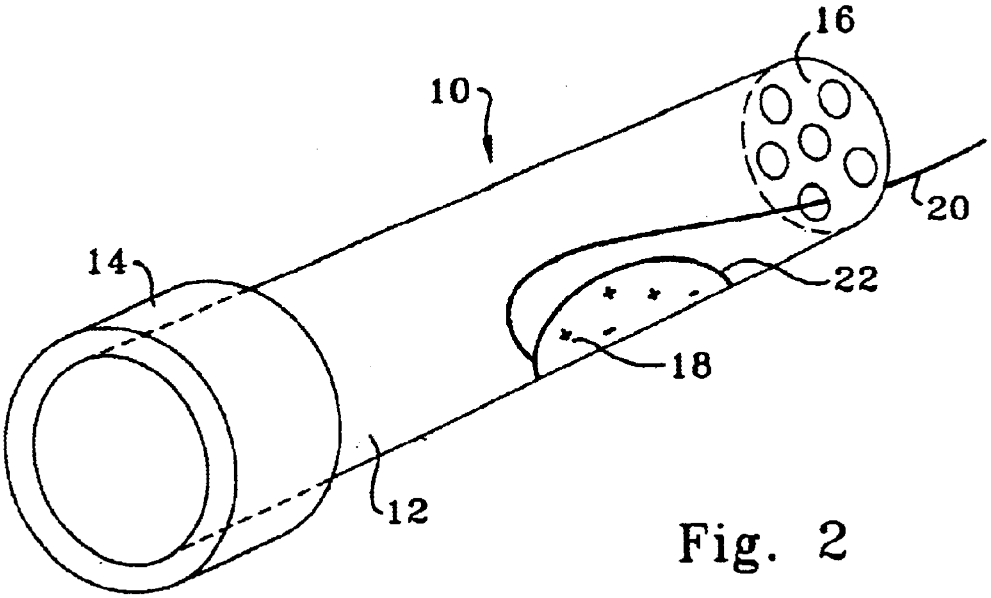
Fig. 2

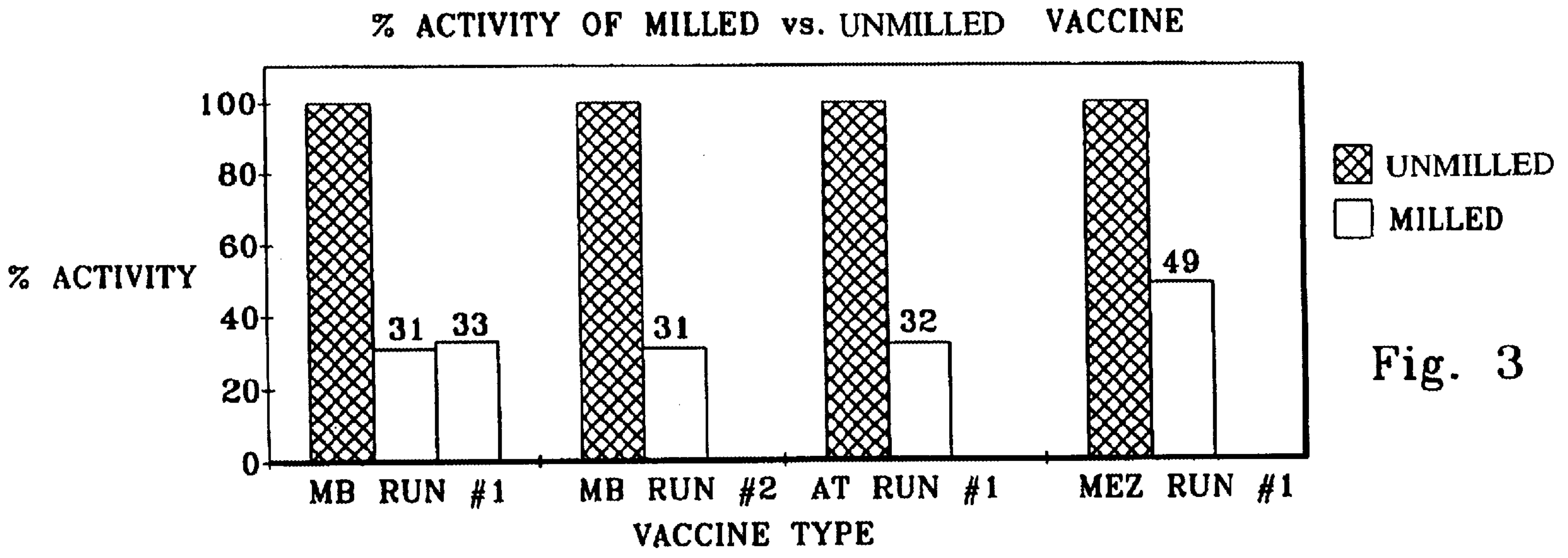
Fig. 3
Fig. 4
SUMMARY OF SIZING DATA (μm) OF JET MILLED MEASLES VACCINE
| | D(v,0.1) | D(v,0.5) | D(v,0.9) |
|---|---|---|---|
| ATTENUVAX | 1.42 | 3.25 | 6.65 |
| | 1.45 | 3.48 | 7.16 |
| MEXICAN EZ | 1.15 | 3.06 | 8.97 |
| | 1.30 | 3.44 | 8.77 |
| | 1.27 | 3.52 | 9.82 |
Fig. 5
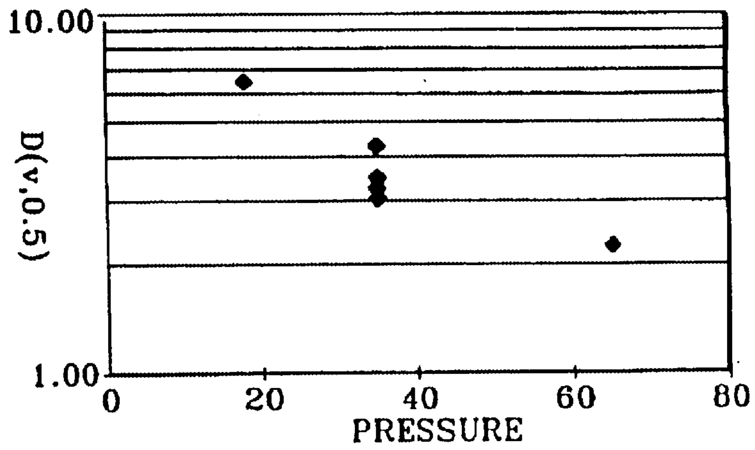

INHALED VACCINES

This application claims priority to U.S. Provisional Application Serial Nos. 60/176,525; 60/176,530; and 60/176,587, all filed on Jan. 18, 2000, and all incorporated herein by reference.

BACKGROUND OF THE INVENTION

The field of the invention is delivery of vaccines.

Bacterial and viral diseases have long plagued mankind. Bacterial diseases include tuberculosis, typhoid, pneumonia, meningitis, pertussis, diphtheria, cholera, streptococcal infections and other disabling or potentially fatal diseases. Some of the more common or better known viral diseases are chicken pox, measles, mumps, rubella, influenza, parainfluenza, hepatitis, HIV/AIDS and the diseases associated with rotavirus, cytomegalovirus, herpes simplex, respiratory syncytial, and Epstein-Barr viruses. Many of these bacterial or viral diseases are highly contagious, difficult to treat or cure, or have treatments or cures involving serious undesirable side effects.

Modern medicine has provided vaccines targeted at many of these bacterial and viral diseases. The vaccines work by inducing the body (human or animal) to produce antibodies, so that the body better resists infection when subsequently exposed to the bacteria or virus. In addition, therapeutic vaccines are currently in development to treat chronic ailments such as autoimmunity, hypertension, cancer and even drug addiction.

Various forms of vaccine have been used to combat these diseases. The common forms of vaccines are live attenuated vaccines, including bacteria and viruses (RNA or DNA-based), killed organism vaccines, polypeptide-based vaccines, polysaccharides, conjugated polysaccharides and inactivated toxins. In addition, vaccines in development include naked DNA vaccines and genetically engineered organisms or hybrids.

Conventionally, vaccines have been prepared as a reconstituted liquid and injected into the patient using a syringe. Unfortunately, this delivery technique has several disadvantages. Initially, delivering a vaccine via injection with a syringe involves the risk inherent in using needles. Specifically, under certain conditions, there is risk of transmission of disease via the injection, due to contamination with blood borne pathogens such as HIV, hepatitis B, HCV, etc. The risk of such contamination is significant, especially in developing countries. The World Health Organization estimates that up to one-third of all injections given in developing countries are unsafe.

Vaccine delivery by injection is often also perceived to be painful, especially by children, thereby resulting in potentially uncooperative patients. Delivery by injection also requires that the practitioner providing the injection have a measure of skill and training.

In efforts to overcome these disadvantages, various proposals have been made for delivering vaccines to the lung with some form of nebulizer or metered-dose inhaler. In these proposals, the liquid suspension vaccine is dispersed into a cloud of tiny droplets, which are then inhaled by the patient. Some of these proposals have recognized the advantages in providing an enhanced local respiratory tract immunity, especially against diseases active in the lungs. Studies on vaccines delivered in nebulized forms show that patient's immune response resulting from delivery of a vaccine to the lung, equals or exceeds the immune response created by vaccine injection.

However, notwithstanding these results, vaccines continue to be delivered primarily via injection, apparently due to reasons of cost, convenience, and complexity of operating metered-dose inhalers and nebulizers.

Accordingly, there is a need for improved methods for providing a vaccine to a patient via the lung, to create an immune response.

SUMMARY OF THE INVENTION

To this end a vaccine is provided as a dry powder formulation, via inhalation. This pulmonary delivery of a vaccine as a dry powder for inhalation has the potential to address several critical issues: (1) the need to increase biological efficacy by providing a vaccine that better confers local mucosal immunity as well as systemic immunity, (2) the need to increase safety during administration by eliminating the potential contamination risks associated with needles, (3) the need to increase stability during administration and transport of vaccines and (4) the need to improve cost effectiveness.

Pulmonary delivery of a 'local' dose refers to topical administration to the lung as is typically used for treatment of respiratory disorders such as chronic obstructive pulmonary disease (COPD), asthma and cystic fibrosis. In the context of immunization, delivery of a local dose of vaccine is appropriate and sufficient to induce protective immunity against pathogens that naturally enter the body via the nose or mouth. Alternatively, a systemic dose typically describes administration via the lung for absorption from the alveolar region to the circulation to treat systemic disorders, such as diabetes, migraine, osteoporosis, and hormone regulation. For example, to generate protection against blood borne pathogens, a systemic dose of vaccine may be required. Increased protection may be achieved by producing a vaccine that targets both local and systemic delivery. The choice or balance achieved between local and systemic dose impacts the approach taken to formulate the dry powder for inhalation. The two main factors to be considered are the anatomy of the lung and aerosol dynamics.

As the airways of the lung become smaller and more highly branched, they become increasingly difficult to penetrate with aerosol. To optimize deposition in either (1) the Oropharyngeal/tracheobronchial region for a local dose or (2) the bronchial/pulmonary region for a systemic dose, a key parameter to control is particle size. It is generally accepted that for particles with aerodynamic diameters less than 5 microns, the greatest fractional deposition is in the bronchial/pulmonary region of the lung. Deposition in the Oropharyngeal/tracheobronchial region occurs with particles ranging from approximately 5 to 100 $\mu$m. For some diseases, such as measles, vaccine particle sizing may not be critical since the CD46 receptors that are recognized by the measles virus are virtually ubiquitous, being expressed by almost all cells except erythrocytes and some bone marrow cells.

BRIEF DESCRIPTION OF THE DRAWINGS

FIG. 1 is a graph of vaccine particle size distribution.

FIG. 2 is a perspective view of a vaccine inhaler

FIG. 3 is a graph of activity of milled and unmilled vaccines

FIG. 4 is a table of sizing data

FIG. 5. is a graph of volume median diameter versus mill air pressure

DETAILED DESCRIPTION OF THE INVENTION

A. Preparation of a Vaccine Formulation

The process of preparing dry powder blends for aerosol delivery involves three basic steps. First, the particles are size reduced to a volume median diameter ranging from 1 to 5 μm or 5 to 100 μm, depending on whether systemic or local delivery is desired. This necessary initial step has discouraged others from trying a dry powder inhaled vaccine in the past. While these techniques appear destructive to the active vaccine substance, we have discovered that biological activity does indeed survive these techniques. Size reduction may be accomplished by a variety of techniques including spray drying, precipitation from supercritical fluids, and jet milling or micronization. Preferably, jet milling is used. This technique uses high pressure, high velocity gas to cause particle to particle attrition to generate small particles at high efficiencies.

For many years, it was believed that proteins would not withstand micronization by air jet milling. However, the process was established as applicable for proteins when six peptides were milled and tested (for systemic delivery) in a (DPI) inhaler as described in U.S. Pat. No. 5,577,497, incorporated herein by reference. Five of the peptides retained biological activity as shown either by direct assay (three peptides) or as inferred by a previously demonstrated correlation between bioactivity and the in vitro assay (two peptides). Biological activity of one peptide was not assessed. For at least one protein which was thoroughly tested, both in vitro assay and direct assay of biological activity surprisingly revealed no difference between milled and unmilled protein.

While the ability of milled proteins to retain activity is unexpected, more surprising is the discovery that a viral vaccine can be processed in this manner. Particle size distribution of milled vaccine powder, as shown in FIG. 1, is measured in liquid suspensions using a laser diffraction instrument. The data in Table 1 below show that micronization of live, attenuated measles vaccine by jet milling generates particle sizes appropriate for pulmonary delivery while maintaining viral potency at levels up to as high as 89%, depending on the milling conditions.

TABLE 1

Retention of Viral Potency for Milled Measles Vaccine

| Milling Conditions | % Potency Retained vs. Unmilled Control | Volume Median Diameter (μm) |
|---|---|---|
| 18 psig | 75 | 6.4 |
| 35 psig | 81 | 3.2 |
| 35 psig cool mill collection vessel | 89 | 4.3 |
| 65 psig | 8.4 | 2.2 |

The discovery that a large (~150–200 nm), lipid-enveloped virus with functionally important transmembrane surface proteins can withstand milling implies that other vaccines, less robust than the paramyxoviruses, should be capable of being processed similarly.

Once small particles have been produced to provide for deep lung deposition, the micronized substance is blended with an excipient, preferably lactose. The lactose particles are large, on the order of 100 μm, or approximately 50 times bigger than the milled vaccine particles. These lactose carrier particles help to facilitate the dispersion of the small particles and allow precise filling into the dry powder inhaler (DPI) powder storage system in a reproducible manner. Milled drug is blended with lactose at concentrations ranging from <1 to 50%. Finally, the blend is filled into the powder storage systems of an inhaler at weights ranging from approximately 3–25 mg. Preferred powder storage systems are shown in U.S. Pat. Nos. 5,492,112; 5,645,051; 5,622,166; and 5,921,237, incorporated herein by reference. The vaccine may also be prepared without any excipient.

The final step, after making the dry powder blend, is to fill the blend into the powder storage systems. The inhaler and storage systems shown in U.S. Pat. Nos. 5,921,237 and 5,622,166, incorporated herein by reference, are appropriate for use with vaccines. In these systems, a dry powder formulation is sealed into a foil blister that protects the powder from exposure to high humidity, reduces the risk of contamination, and can prevent inactivation of the vaccine by sunlight and other ultraviolet sources.

These inhalers provide reproducible dosing that is independent of inspiratory flow rate over a broad range. A high speed rotating impeller aids in powder dispersion. The impeller and battery power make the actual dose received independent of the ability of the patient to inhale vigorously. The fact that the inhaler is breath actuated eliminates the need for patient coordination. The absence of propellants, such as the internationally restricted chlorofluoro-carbons used in many metered dose inhalers, makes the DPI environmentally safe. Other known dispersion mechanisms using, e.g., expanding compressed gases or tortuous paths, and other inhaler designs, such as described in U.S. patent application Ser. No. 09/495,494, incorporated by reference, may also be used.

Multidose DPI inhalers may be used with disposable cassettes or foil blister disks, strips or unit dose blisters to deliver many doses, contributing to the cost effectiveness of this approach as compared with syringes, particularly single use syringes. These DPI's may be provided with disposable mouthpieces that can be used in mass vaccination campaigns. Alternatively, unit dose DPIs with vaccine sealed in the aerosolization chamber can be used. A disposable unit dose inhaler 10 is shown in FIG. 2. The inhaler 10 has a tubular body 12 and a mouthpiece 14. A restrictor plate 16 having flow control openings is optionally provided in the tubular body 12, opposite from the mouthpiece. A dose of dry powder vaccine 18 is sealed by a foil strip 20 within the body 12. In use, the foil strip 20 is pulled out or back, peeling or breaking open blister 22 formed around the dose 18. The patient inhales on the mouthpiece, and the dose is drawn into the lungs. The inhaler and dose characteristics are selected as described above.

B. Advantages of Vaccine Delivery by Dry Powder Inhaler Include:

1. Minimal escape of viral particles into the environment during use as compared to liquid nebulization.
2. Reduction or elimination of the necessity to keep the vaccine material under refrigeration.
3. Doses may be administered by nonmedical personnel.
4. Reduced risk of contamination.

C. Measles Vaccine

While the principles of the invention apply to many different vaccines, significant testing has been performed on measles vaccines.

Currently, measles vaccine is stored and shipped as a lyophilized powder, then reconstituted with diluent for injection. Previous aerosol delivery approaches have used reconstituted measles vaccine. An advantage of a dry powder formulation is the significant difference in stability of the reconstituted versus the lyophilized vaccine. Reconstituted measles vaccine loses potency rapidly at both 25 and 37° C.

At 37° C., between 30–50% loss in potency occurs within 1 hour as compared with ~0.4% loss/h for the lyophilized vaccine. To improve thermostability of the reconstituted vaccine, it must be kept cold, which is often achieved in aerosol studies by placing the nebulizer with reconstituted vaccine on crushed ice. Use of the present dry powder measles vaccine formulation eliminates the cold chain requirement during immunization. In current practice, temperatures between 0–8° C. are needed throughout all phases of storage and shipping to comply with manufacturer's recommendations. Eliminating the cold chain requirement during the last leg of transport to final-destination health centers and remote locations would greatly facilitate measles eradication efforts.

The optimal site to target measles vaccine delivery is the lung, to mimic a natural route of measles transmission, and thus potentially produce superior local respiratory tract immunity. The intent in developing a dry powder formulation is to increase ease of administration (noninjectable), reduce refrigeration requirements (dry powder), reduce risk of contamination and maintain a reasonable cost. The method is noninvasive, nontraumatic and avoids the risk of transmitting hepatitis B, HIV and other agents through improper injection practices. Finally, a dry powder formulation can be delivered from an inhaler that can withstand the rigors of transport and use in mass vaccination campaigns and, most importantly, ensure efficient, reproducible dosing. The need for reconstitution before use is eliminated, thereby enhancing the room temperature stability.

The calculation of predicted blend concentrations of a dry powder formulation using measles vaccine is shown in Table 2 below:

TABLE 2

| Vaccine Titer (log 10) | $TCID_{50}$/mg[(a)] | Blend % 3 mg fill wt.[(b,c)] | Blend % 25 mg fill wt[(b,c)] | Dose to Lung ($TCID_{50}$) |
|---|---|---|---|---|
| 5.6 | 13270 | 13% | 1.6% | 1000 |
| 5.1 | 4196 | 42% | 5% | 1000 |
| 4.7 | 1671 | N/A[d] | 13% | N/A[d]–1000 |
| 4.5 | 1054 | N/A[d] | 20% | N/A[d]–1000 |

[(a)]Based on 30 mg of vaccine per single dose
[(b)]Assuming 75% potency retention after milling
[(c)]Assuming 25% delivery efficiency
[(d)]Vaccine concentration greater than 50% of formulation Commonly, measles vaccines have titers ranging from $10^{3.5}$ to $10^{4.5}$ $TCID_{50}$ (tissue culture infective dose, 50%) However, in some studies the vaccine has been supplied with titers routinely as high as $10^{4.7}$ to $10^{5.6}$ $TCID_{50}$. The studies performed with nebulized vaccine provide evidence for the assumption that an aerosol dose to the lung need not be greater than the currently accepted minimum subcutaneous dose of 1000 $TCID_{50}$. Using values for emitted dose and respirable fraction typically seen with the DPI described in U.S. Pat. No. 5,577,497, and other formulated drug products, Table 2 shows the range of vaccine concentrations that could be formulated as a powder for inhalation. While this suggests measles vaccine concentrations ranging from approximately 1–50% in lactose, some of the studies with nebulized measles vaccine achieved seroresponse with remarkably low doses. Therefore, the dose requirement for pulmonary delivery may be made even lower.

The vaccines are provided as lyophilized powder in sealed ampoules and are tested for potency before and after jet milling at 35 psig. Results are shown in FIG. 3. Unmilled samples represent those that were opened and exposed to the same conditions of relative humidity as milled samples. Viral activity is reported as plaque forming units (pfu) and is normalized to the weight of the powder sample.

Experimentally, another challenge in milling is that the vaccines are hygroscopic. This characteristic appears to be due to the excipients and/or stabilizers used in the lyophilization process rather than the virus itself, since measles vaccines from different manufacturers have varying degrees of hygroscopicity. This challenge was met by milling in a glove box at 2.3% relative humidity.

Despite low initial titers and a difference in the initial activity between Moraten Berna (MB), Attenuvax (AT), and Mexican EZ, % potency retentions are similar. After milling, MB and AT samples retain roughly 31% activity and MEZ retains 49% activity as compared with unmilled samples, as shown in FIG. 3.

For the examples shown in FIG. 3, conditions were not optimized for maximal potency retention. Still, even in cases where the micronization parameters are not optimized, the 31% activity that remains after milling represents a product with significant advantage over those that require reconstitution. Second, high titer vaccines may be used in the process to ultimately deliver the standard dose to the recipient. Third, immunization by aerosol may require a smaller dose than immunization by injection. Studies with nebulized measles vaccine have demonstrated high rates of seroconversion with doses much lower than the 1000 $TCID_{50}$ presently required. Finally, milled vaccine that contains a mix of live and non-viable virus may still be highly immunogenic and effective in conferring humoral and mucosal immunity.

Seventy percent of the vaccine (by volume) has particle sizes less than 5 μm, an appropriate size for pulmonary delivery. Even more important for vaccine delivery, the number of viral particles less than 5 μm is ~90%. Particle size is typically reported as volume median diameter, D(v, 0.1), D(v, 0.5), D(v, 0.9) refers to particle diameters below which 10%, 50%, or 90% of the sample volume is contained. Particle size data for the Attenuvax and Mexican EZ vaccines milled at 35 psi are summarized in FIG. 4.

FIG. 5 shows the relationship between pressure and particle size reduction for milled measles vaccine. The somewhat linear relationship between the variables, when plotted on a log normal scale, indicates a process with a level of predictability.

Mexican EZ measles vaccine milled at 35 psig was subsequently blended with lactose to a final concentration of 10%. This blend served as starting material for preliminary evaluation of dispersability and aerosol characteristics. Blend uniformity was tested by the plaque assay (data not shown).

Thus, novel compositions and methods have been described. Various changes may of course be made, without departing from the spirit and scope of the invention. The invention, therefore, should not be limited, except by the following claims and their equivalents.

What is claimed is:

1. A method for creating an immune response in a patient, comprising the steps of:

preparing a vaccine material as a vaccine formulation including dry powder vaccine particles, with at least 90% of the dry powder vaccine particles having an aerodynamic particle size of less than 100 microns;

loading the vaccine formulation into a dry powder inhaler free of any propellant gas; and disbursing the dry powder vaccine particles and inhaling the vaccine particles, via patient inspiration at an inspiratory flow rate of less than 10 liters per minute.

2. The method of claim 1 further including the step of allowing at least some of the dry powder vaccine particles in the vaccine formulation to deposit on the oropharynx, trachea and upper bronchial region of the lungs of the patient.

3. The method of claim 1 wherein at least 90% of the dry powder vaccine particles have an aerodynamic particle size of less than 50 microns.

4. The method of claim 1 where at least 90% of the dry powder vaccine particles have an aerodynamic diameter of less than 10 microns.

5. The method of claim 1 where at least 90% of the dry powder vaccine particles have an aerodynamic diameter of less than 5 microns.

6. The method of claim 1 wherein the patient inhales with an inspiratory effort through the dry powder inhaler which does not exceed 10 Joules.

7. The method of claim 1 wherein the patient inhales with an inspiratory effort through the dry powder inhaler does not exceed 6 Joules.

8. The method of claim 1 wherein the patient inhales with an inspiratory effort through the dry powder inhaler does not exceed 4 Joules.

9. The method of claim 1 wherein the vaccine material comprises at least one member selected from the group consisting of live attenuated vaccines including bacteria and viruses (RNA or DNA-based), killed organism vaccines, polypeptide-based vaccines, polysaccharides, conjugated polysaccharides, inactivated toxins, naked DNA vaccines and genetically engineered organisms or hybrids.

10. The method of claim 9 wherein the vaccine material further comprises an excipient.

11. The method of claim 1 wherein the vaccine material provides an immune response to the following diseases and/or pathogens: tuberculosis; streptococcus (groups A and B); respiratory syncytial virus; herpes simplex; varicella; typhoid; influenza; parainfluenza, measles; mumps; rubella; pertussis; pneumonia; meningitis; diphtheria; Epstein-Barr virus; cytomegalovirus; cholera; rotavirus; hepatitis; autoimmune disease; hypertension, cancer, and substance addiction.

12. The method of claim 11 wherein the immune response is to the measles and an inhaled dose is from 3–25 mg.

13. The method of claim 12 wherein the inhaled dose is from 6–10 mg.

14. The method of claim 12 wherein the vaccine formulation includes a concentration of the vaccine material ranging from 1–50% with a balance being lactose.

15. A method for delivering measles vaccines comprising the steps of:

reducing the measles vaccines to a volume of measles vaccine particles with a median diameter of from 1–5 micron;

blending the measles vaccine particles with an excipient to form a blended formulation;

filling a single dose of the blended formulation into a blister container; and sealing the blister container;

opening the blister container at a time of delivering the measles vaccine;

disbursing the blended formulation for inhalation via patient inspiration; and inhaling the disbursed blended formulation into the lungs of a patient; wherein the measles vaccine retains a sufficient potency to provide an immune response.

16. The method of claim 15 wherein the measles vaccines are reduced by a spray drying, a precipitation, a freeze spray drying, a supercritical fluid drying, a grinding, a jet milling or a micronization.

17. The method of claim 15 wherein the measles vaccines are reduced by a jet milling and with a jet milling pressure low enough to retain at least 31% potency after the jet milling.

18. The method of claim 17 wherein the jet milling is performed in a collection vessel, and further comprising the step of cooling the collection vessel to increase a retained potency.

19. An inhaler for delivering a vaccine comprising:

an inhaler body;

a mouthpiece on the inhaler body;

a dose container on or in the inhaler body;

a dry powder formulation, including dry powder vaccine particles with at least 90% of the dry powder vaccine particles having an aerodynamic particle size of less than 100 microns, within the dose container;

a seal on the dose container, sealing the dry powder formulation in the dose container; and the inhaler body and the mouthpiece having a flowpath therethrough, with the flowpath having a flow resistance of from 0.1–0.25 $(cmH_2O)^{1/2}$/liter per minute, to provide for powder disbursion and inhalation via patient inspiration.

20. The method of claim 19 wherein the dry powder formulation is inhaled with from 1–10 inspirations.

21. A vaccine dose comprising:

a vaccine material as a vaccine formulation including dry powder vaccine particles, with at least 90% of the dry powder vaccine particles having an aerodynamic particle size of less than 100 microns; and the vaccine dose having a weight of from 3–25 mg, with the vaccine dose contained in a sealed container adapted to be opened with the use of a dry powder inhaler, to allow a user to inhale the dose.

22. The vaccine dose of claim 21 wherein the dry powder vaccine particle have been obtained by a spray drying; a freeze spray drying; a precipitation; a supercritical fluid drying; a jet milling; or a micronization.

23. The vaccine dose of claim 22 with the vaccine material having at least 31% potency.

24. The vaccine dose of claim 22 further including an excipient.

25. The vaccine dose of claim 22 where the vaccine material is at least one member selected from the group consisting of live attenuated vaccines including bacteria and viruses (RNA or DNA-based), killed organism vaccines, polypeptide-based vaccines, polysaccharides, conjugated polysaccharides, inactivated toxins, naked DNA vaccines and genetically engineered organisms or hybrids.

26. A method for creating an immune response in a patient, comprising the steps of:

preparing a vaccine material as a vaccine formulation including dry powder vaccine particles with at least 90% of the dry powder vaccine particles having an aerodynamic particle size of less than 5 microns;

loading the vaccine formulation into a propellant gas-free dry powder inhaler;

disbursing the vaccine material via air flow induced by inhalation;

inhaling the vaccine formulation; and allowing at least some of the dry powder vaccine particles in the vaccine formulation to deposit on the pulmonary and the bronchial region of the lungs of the patient to provide both systemic and local mucosal immunity.

27. The method of claim 26 where at least 90% of the dry powder vaccine particles have an aerodynamic diameter of less than 10 microns.

28. The method of claim 27 where at least 90% of the dry powder vaccine particles have an aerodynamic diameter of less then 5 microns.

29. A method for creating an immune response in a patient, comprising the steps of:

micronizing a vaccine material to form dry powder vaccine particles, with at least 90% of the dry powder vaccine particles having an aerodynamic particle size of less than 25 microns, while retaining at least 31% potency;

blending the vaccine material with lactose particles larger than the vaccine particles into a blended formulation;

loading the blended formulation into a propellant gas-free dry powder inhaler; and disbursing and inhaling the blended formulation, wherein the patient's inspiratory flow rate is less than 10 liters/minute, and wherein the inhaled dose is 3–25 mg.

* * * * *